(12) United States Patent
Wang et al.

(10) Patent No.: US 11,292,889 B2
(45) Date of Patent: Apr. 5, 2022

(54) BENZOPHENONE DERIVATIVE, AQUEOUS COPOLYMER DISPERSION AND AQUEOUS COATING COMPOSITION

(71) Applicants: Dow Global Technologies LLC, Midland, MI (US); Rohm and Haas Company, Collegeville, PA (US)

(72) Inventors: Yujiang Wang, Shanghai (CN); Hui Liu, Shanghai (CN); Caifeng Wang, Shanghai (CN); Jianming Xu, Shanghai (CN); Ling Li, Shanghai (CN); Alvin M. Maurice, Lansdale, PA (US); Hongyu Chen, Shanghai (CN)

(73) Assignees: Dow Global Technologies LLC, Midland, MI (US); Rohm and Haas Company, Collegeville, PA (US)

(*) Notice: Subject to any disclaimer, the term of this patent is extended or adjusted under 35 U.S.C. 154(b) by 580 days.

(21) Appl. No.: 16/317,860

(22) PCT Filed: Aug. 17, 2016

(86) PCT No.: PCT/CN2016/095677
§ 371 (c)(1),
(2) Date: Jan. 15, 2019

(87) PCT Pub. No.: WO2018/032410
PCT Pub. Date: Feb. 22, 2018

(65) Prior Publication Data
US 2021/0347963 A1 Nov. 11, 2021

(51) Int. Cl.
| | | |
|---|---|---|
| C08K 5/18 | (2006.01) | |
| C09D 7/63 | (2018.01) | |
| C08L 33/08 | (2006.01) | |
| C09D 133/08 | (2006.01) | |

(52) U.S. Cl.
CPC .............. *C08K 5/18* (2013.01); *C08L 33/08* (2013.01); *C09D 7/63* (2018.01); *C09D 133/08* (2013.01); *C08L 2201/50* (2013.01); *C08L 2201/52* (2013.01)

(58) Field of Classification Search
CPC .......... C08K 5/18; C09D 7/63; C09D 133/08; C08L 33/08; C08L 2201/50; C08L 2201/52
USPC ........................................................ 524/248
See application file for complete search history.

(56) References Cited

U.S. PATENT DOCUMENTS

| | | | |
|---|---|---|---|
| 6,133,401 | A | 10/2000 | Jensen |
| 6,376,570 | B1 | 4/2002 | Zhao et al. |
| 9,604,391 | B2 | 3/2017 | Tamada et al. |
| 2006/0293404 | A1 | 12/2006 | Santobianco et al. |
| 2007/0293588 | A1 | 12/2007 | Yoshida et al. |
| 2011/0074897 | A1* | 3/2011 | Araki ............... C09D 11/101 347/102 |
| 2011/0245390 | A1 | 10/2011 | Yang et al. |

FOREIGN PATENT DOCUMENTS

| | | |
|---|---|---|
| CA | 2479942 A1 | 11/2003 |
| CA | 2903724 A1 | 9/2014 |
| CN | 102516867 A | 6/2012 |
| CN | 103146331 A | 6/2013 |
| CN | 103834343 A | 6/2014 |
| CN | 104531024 A | 4/2015 |
| CN | 105524546 A | 4/2016 |
| DE | 4318083 A1 | 5/1994 |
| EP | 1496091 A1 | 1/2005 |
| EP | 2371913 A1 | 10/2011 |
| JP | 2005019026 A | 1/2005 |
| JP | 2006137882 A | 6/2006 |

OTHER PUBLICATIONS

Brandrup, J., Immergut, E. H., Grulke, E. A. (Editors); Glass Transition Temperatures of Polymers, Polymer Handbook, 4th Edition, Interscience Publishers, 1999.
European Search Report for European Application No. 16913170.3 dated Dec. 20, 2019, 9 pages.
Kricheldorf, H. R. et al., "New polymer syntheses. 41. Synthesis of thermoplastic aromatic poly(ether amides) from silylated aminophenols", European Polymer Journal, 1990, vol. 26, No. 7, pp. 791-797.
International Search Report for International Application No. PCT/CN2016/095677, International Filing Date Aug. 17, 2016, dated Mar. 24, 2017, 4 pages.
Written Opinion for International Application No. PCT/CN2016/095677, International Filing Date Aug. 17, 2016, dated Mar. 24, 2017, 3 pages.

* cited by examiner

*Primary Examiner* — Hui H Chin
(74) *Attorney, Agent, or Firm* — Karl E. Stauss; Cantor Colburn LLP

(57) ABSTRACT

The present invention relates to a benzophenone derivative and an aqueous copolymer dispersion comprising the benzophenone derivative. This invention also relates to an aqueous coating composition comprising the aqueous copolymer dispersion. The benzophenone derivative provides better crosslinking efficiency and improvement to dirt pick up resistance performance.

6 Claims, No Drawings

BENZOPHENONE DERIVATIVE, AQUEOUS COPOLYMER DISPERSION AND AQUEOUS COATING COMPOSITION

FIELD OF THE INVENTION

The present invention relates to a benzophenone derivative, and an aqueous copolymer dispersion comprising the benzophenone derivative. This invention also relates to an aqueous coating composition comprising the aqueous copolymer dispersion.

BACKGROUND

Dirt pick up resistance (DPUR) of a coating is the ability to minimize accumulation of dirt, dust, soot and other such materials on the surface of the coating. A coating with poor DPUR performance usually has an unclean and darkened appearance.

A conventional approach to improve the DPUR performance of coatings is by using benzophenone as a photo initiator in coating applications. Upon ultraviolet (UV) light exposure occurs benzophenone photochemistry which is UV light-induced crosslinking reactions of polymers. This conventional approach may exploit sunlight as a UV sources at low cost. However, there are some drawbacks with benzophenone. Benzophenone is less effective in improving DPUR performance over a long period of time. The crosslinking effect caused by benzophenone photochemistry will also be heavily reduced in rainy conditions during applications. Coating film surfaces are susceptible to cracking due to over crosslinking caused by high dosing levels of benzophenone. Benzophenone easily sublimates, which may lead to volatile organic compounds (VOC) emission.

To improve long term DPUR performance, benzophenone derivatives are used as light stabilizing additives in combination with benzophenone. However, due to the presence of benzophenone, VOC emission remains a concern.

Therefore, it is desirable to provide a novel benzophenone derivative as a replacement of benzophenone and the combination of benzophenone and benzophenone derivatives, which novel benzophenone derivative provides better crosslinking efficiency and improvement to DPUR performance.

SUMMARY OF THE INVENTION

In a first aspect, the present invention provides a benzophenone derivative represented by the following Formula A:

[Formula A]

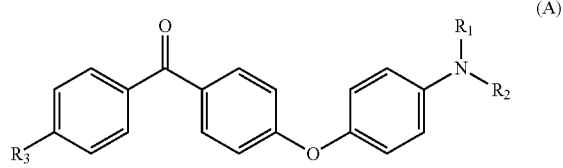

(A)

wherein $R_1$ and $R_2$ are each independently hydrogen, alkyl or a substituted alkyl group, and $R_3$ is hydrogen or has a structure of Formula B:

[Formula B]

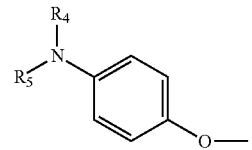

(B)

wherein $R_4$ and $R_5$ are independently hydrogen, alkyl, or a substituted alkyl group.

In a second aspect, the present invention provides an aqueous copolymer dispersion comprising (a) an aqueous emulsion copolymer, wherein the aqueous emulsion copolymer comprises, as copolymerized units, at least 90% by weight, based on the dry weight of the copolymer, of an ethylenically unsaturated nonionic monomer; and up to 10% by weight, based on the dry weight of the copolymer, of an ethylenically unsaturated stabilizer monomer; and (b) from 0.05% to 3% by weight, based on the dry weight of the copolymer, of the benzophenone derivative of the first aspect.

In a third aspect, the present invention provides an aqueous coating composition comprising the aqueous copolymer dispersion of the second aspect.

DETAILED DESCRIPTION OF THE INVENTION

The benzophenone derivative represented by the following Formula A:

[Formula A]

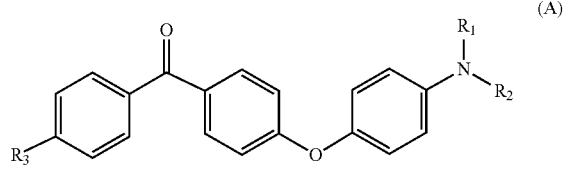

(A)

wherein $R_1$ and $R_2$ are each independently hydrogen, alkyl or a substituted alkyl group, and $R_3$ is hydrogen or has a structure of Formula B:

[Formula B]

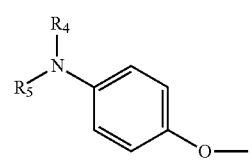

(B)

wherein $R_4$ and $R_5$ are independently hydrogen, alkyl, or a substituted alkyl group.

The benzophenone derivative of the present invention may be prepared by a conventional substitution reaction. In one embodiment, the benzophenone derivative may be synthesized by reacting 4-hydroxyaniliane with 4-chloro benzophenone or 4,4'-dichloro benzophenone in the presence of one or more strong base catalyst at a temperature of from about 120° C. (degree Celsius) to 180° C. As used in this specification, a strong base catalyst is an inorganic hydroxide. Examples of suitable strong base catalysts include sodium hydroxide, potassium hydroxide; or combinations thereof. Preferably, the strong base catalyst is sodium hydroxide.

The aqueous copolymer dispersion comprises:

(a) an aqueous emulsion copolymer, wherein the aqueous emulsion copolymer comprises, as copolymerized units, at least 90% by weight, based on the dry weight of the copolymer, of an ethylenically unsaturated nonionic monomer; and up to 10% by weight, based on the dry weight of the copolymer, of an ethylenically unsaturated stabilizer monomer; and (b) from 0.05% to 3%, preferably from 0.1% to 1%, and more preferably from 0.2% to 0.8% by weight, based on the dry weight of the copolymer, of the benzophenone derivative of the present invention.

The term "at least" in a percentage range herein means any and all amounts greater than and including the start point of the range through to 100% but not including 100%.

The term "up to" in a percentage range herein means any and all amounts larger than zero and through to and including the end point of the range.

By "nonionic monomer" herein is meant that the copolymerized monomer residue does not bear an ionic charge between pH=1-14. The ethylenically unsaturated nonionic monomers include, for example, (meth)acrylic ester monomers, wherein "(meth)acrylic ester" designates methacrylic ester or acrylic ester, including methyl acrylate, ethyl acrylate, butyl acrylate, 2-ethylhexyl acrylate, decyl acrylate, lauryl acrylate, methyl methacrylate, butyl methacrylate, isodecyl methacrylate, lauryl methacrylate, hydroxyethyl methacrylate, hydroxypropyl methacrylate; (meth)acrylonitrile; amino-functional and ureido-functional monomers; monomers carrying alkoxysilane functionality; monomers bearing acetoacetate-functional groups; styrene and substituted styrenes; butadiene; ethylene, propylene, α-olefins such as 1-decene; vinyl acetate, vinyl butyrate, vinyl versatate and other vinyl esters; and vinyl monomers such as vinyl chloride, vinylidene chloride.

By "stabilizer monomer" herein refers to the copolymerized monomer residue bears an ionic charge between pH=1-14. The stabilizer monomer includes, for example, α,β-monoethylenically unsaturated carboxylic acids of from 3 to 8 carbon atoms, anhydrides and amides. The α,β-monoethylenically unsaturated carboxylic acid monomers include, for example, acrylic acid, methacrylic acid, crotonic acid, itaconic acid, maleic acid and salts or anhydrides thereof, and the amides of these acids, particularly acrylamide and methacrylamide; and combinations thereof. The stabilizer monomer further includes sulfur-containing or phosphor-containing acidic monomer.

In one embodiment, the aqueous emulsion copolymer may further comprise up to 5%, preferably up to 3%, more preferably up to 2% by weight, based on the dry weight of the copolymer, of copolymerized multi-ethylenically unsaturated monomers, for example, allyl methacrylate, diallyl phthalate, 1,4-butylene glycol dimethacrylate, 1,2-ethylene glycol dimethacrylate, 1,6-hexanediol diacrylate, or divinyl benzene; or combinations thereof.

In one embodiment, the aqueous emulsion copolymer has a glass transition temperature (Tg) of −70° C. to +70° C., preferably from −40° C. to +30° C.

"Tg" used herein are those calculated by using the Fox equation (T. G. Fox, Bull. American Physical Society, Volume 1, Issue No. 3, page 123 (1956)). For example, for calculating the Tg of a copolymer of monomers $M_1$ and $M_2$, $$\frac{1}{T_g(calc.)} = \frac{w(M_1)}{T_g(M_1)} + \frac{w(M_2)}{T_g(M_2)},$$

wherein Tg (calc.) is the glass transition temperature calculated for the copolymer, $w(M_1)$ is the weight fraction of monomer $M_1$ in the copolymer, $w(M_2)$ is the weight fraction of monomer $M_2$ in the copolymer, $Tg(M_1)$ is the glass transition temperature of the homopolymer of $M_1$, and $Tg(M_2)$ is the glass transition temperature of the homopolymer of $M_2$, all temperatures being in K. The glass transition temperatures of homopolymers may be found, for example, in "Polymer Handbook", Fourth edition edited by J. Brandrup, E. H. Immergut, and E. A. Grulke, Interscience Publishers, 1999.

The aqueous emulsion copolymer of the present invention may be prepared by polymerization techniques well known in the art. Either thermal or redox initiation processes may be used in the polymerization process. Conventional free radical initiators may be used such as hydrogen peroxide, t-butyl hydroperoxide, t-amyl hydroperoxide, ammonium and alkali persulfates, typically at a level of 0.01% to 3.0% by weight, based on the weight of total monomer. Redox systems using the same initiators coupled with a suitable reductant such as sodium sulfoxylate formaldehyde, sodium hydrosulfite, isoascorbic acid, hydroxylamine sulfate and sodium bisulfite may be used at similar levels, optionally in combination with metal ions such as iron and copper, optionally further including complexing agents for the metal. The monomer mixture may be added in a single addition or more additions or continuously over the reaction period using a uniform or varying composition. Additional ingredients such as oxidants, reducing agents, chain transfer agents, neutralizers, surfactants, and dispersants may be added prior to, during, or subsequent to the monomer addition.

In another embodiment of the present invention, the aqueous emulsion copolymer may be prepared by a multi-stage emulsion polymerization process, in which at least two stages differing in composition are polymerized in sequential fashion. The polymerization techniques used to prepare such multistage emulsion polymers are well known in the art. Such a process sometimes results in the formation of at least two mutually incompatible polymer compositions, thereby resulting in the formation of at least two phases within the polymer particles. Such particles are composed of two or more phases of various geometries or morphologies such as, for example, core/shell or core/sheath particles, core/shell particles with shell phases incompletely encapsulating the core, core/shell particles with a multiplicity of cores, and interpenetrating network particles. In all of these cases the majority of the surface area of the particle will be occupied by at least one outer phase and the interior of the particle will be occupied by at least one inner phase. Each of the stages of the multi-staged emulsion polymer may contain the same monomers, surfactants, chain transfer agents, etc. as disclosed herein-above for the emulsion polymer. In the case of a multi-staged polymer particle, the Tg for the purpose of this invention is to be calculated by the Fox equation as detailed herein using the overall composition of the emulsion polymer without regard for the number of stages or phases therein. Similarly, for a multi-staged polymer particle, the amount of the monomers shall be determined from the overall composition of the emulsion polymer without regard for the number of stages or phases therein.

The average particle diameter of the aqueous emulsion copolymer particles is from 50 to 800 nanometers, preferably from 100 to 400 nanometers, as measured by a BI-90 Particle Sizer.

The aqueous coating composition comprises an aqueous copolymer dispersion comprising, (a) an aqueous emulsion copolymer, wherein the emulsion copolymer comprises, as copolymerized units, at least 90% by weight, based on the dry weight of the copolymer, of an ethylenically unsaturated nonionic monomer; and up to 10% by weight, based on the dry weight of the copolymer, of an ethylenically unsaturated stabilizer monomer; and (b) from 0.05% to 3%, preferably from 0.1% to 1%, and more preferably from 0.2% to 0.8% by weight, based on the dry weight of the copolymer, of the benzophenone derivative of the present invention.

The aqueous coating composition may further comprise at least one coating adjuvant. The adjuvant herein refers to components in the coating except for the emulsion copolymer.

The adjuvant may comprise pigment. Examples of suitable pigments include zinc oxide, antimony oxide, zirconium oxide, chromium oxide, iron oxide, lead oxide, zinc sulfide, lithopone, and titanium dioxide, for example, anatase and rutile titanium dioxide. It is also contemplated that the aqueous copolymer dispersion optionally contains opaque polymer particles such as ROPAQUE™ opaque polymers available from Rohm and Haas Company, a wholly owned subsidiary of The Dow Chemical Company.

The adjuvant may comprise at least one extender. Examples of suitable extenders include calcium carbonate, calcium sulfate, barium sulfate, mica, clay, calcined clay, feldspar, nepheline, syenite, wollastonite, diatomaceous earth, alumina silicates, non-film forming polymer particles having glass transition temperatures above 35° C., aluminum oxide, silica sol and talc.

The adjuvant may comprise colorant. Examples of suitable colorants include inorganic colorant particles and organic colorant particles. Examples of suitable inorganic colorant particles include, for example, iron oxides, chromium oxides, carbon black, and metal effect pigments such as aluminum, copper, copper oxide, bronze, stainless steel, nickel, zinc, and brass. Examples of suitable organic colorant particles include, for example, azo pigments, phthalocyanine pigments, and quinacridone pigments.

Other materials are optionally included in the adjuvants including rheology modifier, coalescents, solvents, biocides, wetting agents, defoamers, dyes, humectants, waxes, surfactants, flatting agents, neutralizers, buffers, free-thaw additives, plasticizers, antifoaming agents, tackifiers, hindered amine light stabilizers, photoabsorbers, dispersants, and anti-oxidants. The photoabsorbers can be combined with the aqueous copolymer dispersion or can be added to the aqueous coating composition subsequently. Suitable levels of photoabsorbers include from 0.1% to 7% by weight solids basis of the aqueous copolymer dispersion.

The amount of pigment and extender in the aqueous coating composition vary from a pigment volume concentration (PVC) of 0 to 85% and thereby encompass coatings otherwise described in the art, for example, clean coatings, flat coatings, satin coatings, semi-gloss coatings, gloss coatings, primers, textured coatings, and the like. Preferable PVC is from 10% to 70%, more preferably PVC is from 10% to 60%. The pigment volume concentration is calculated by the following formula:

$$PVC(\%) = \frac{\text{Volumes of Pigment(s)} + \text{Volumes of Extender(s)}}{\text{Total Dry Volumes of Paint}} * 100$$

If the aqueous copolymer dispersion is to be pigmented, at least one pigment is dispersed in an aqueous medium, preferably using a high shearing mixing. Alternatively, at least one pre-dispersed pigment may be used. In one method, the aqueous copolymer dispersion is added to a pigment dispersion, either simultaneously or sequentially, by mixing under low shear stirring along with other adjuvants as desired, to provide a pigmented aqueous copolymer dispersion. Alternatively, pigment slurry may be prepared in the presence of the aqueous copolymer dispersion.

The solids content of the aqueous coating composition is typically in the range of from 25% to 60% by volume. The viscosity of the aqueous coating composition is typically from 50 KU (Krebs Units) to 140 KU as measured by using a Brookfield Digital Viscometer KU-1. The viscosities appropriate for different application methods vary considerably.

The aqueous coating composition of the present invention may be prepared by techniques which are well known in the coatings art. Components in the aqueous coating composition may be mixed in any order to provide the aqueous coating composition of the present invention. Any of the above-mentioned optional components may also be added to the composition during or prior to the mixing to form the aqueous coating composition.

The process of using the aqueous coating composition of the present invention may comprise the following: applying the aqueous coating composition to a substrate, exposing the applied aqueous coating composition to UV light, and drying the applied aqueous coating composition or allowing it to dry. The aqueous coating composition of the present invention can be applied to a substrate by known means such as brushing, dipping, rolling and spraying. The coating composition is preferably applied by spraying. The standard spray techniques and equipment for spraying such as air-atomized spray, air spray, airless spray, high volume low pressure spray, and electrostatic spray such as electrostatic bell application, and either manual or automatic methods can be used. After the aqueous coating composition of the present invention has been applied to a substrate, the aqueous coating composition may be dried, or be allowed to dry, at a room temperature of from 21° C. to 25° C., or at an elevated temperature, for example, from 35° C. to 60° C. to form a film.

The aqueous coating composition of the present invention can be applied to, and adhered to, various substrates. Examples of suitable substrates include wood, metals, plastics, foams, stones, elastomeric substrates, glass, fabrics, or concrete.

The dry coating prepared from the aqueous coating composition may be used as a protective coating or an aesthetic coating. Examples of suitable coatings include architectural coatings such as interior and exterior paint coatings, including masonry coatings, wood coating, cementious coatings and treatments; maintenance coatings such as metal coatings; paper coatings; and traffic coatings such as those coatings used to provide markings on roads, pavements, and runways.

In the present specification, the technical features in each preferred technical solution and more preferred technical solution can be combined with each other to form new technical solutions unless indicated otherwise. For briefness, the Applicant omits the descriptions for these combinations. However, all the technical solutions obtained by combining these technical features should be deemed as being literally described in the present specification in an explicit manner.

EXAMPLES

The experimental methods in the examples, when not described in detail, is contemplated to follow normal conditions in the art, for example, handbooks of polymer chemistry, or follow conditions suggested by chemical or instrument manufacturer.

I. Raw Materials Used

TABLE 1 to 3 below list the representative materials that can be used to make the benzophenone derivatives, the aqueous copolymer dispersions and the aqueous coating compositions in accordance with certain embodiments of the present invention.

TABLE 1

Representative List of Raw Materials Used to Prepare Benzophenone Derivatives

| Raw material | Function | Supplier |
|---|---|---|
| 4-chloro benzophenone | Reagent | Jintan Chenghong Chemical Factory, China |
| 4-hydroxyaniliane | Reagent | Sinopharm Chemical Reagent Co., Ltd. |
| potassium hydroxide | Catalyst | Sinopharm Chemical Reagent Co., Ltd. |
| N-Methy1-2-pyrrolidone (NMP) | Solvent | Sinopharm Chemical Reagent Co., Ltd. |
| 4,4'-dichloro benzophenone | Reagent | Jintan Chenghong Chemical Factory, China |

TABLE 2

Representative List of Materials Used to Prepare Aqueous Copolymer Dispersions

| Material | Function | Chemical nature | Supplier |
|---|---|---|---|
| PRIMAL ™ AC-261P | Binder | Acrylic polymer | The Dow Chemical Company |
| ELASTENE ™ 3808 | Binder | Acrylic polymer | The Dow Chemical Company |

TABLE 3

Representative List of Materials Used to Prepare Aqueous Coating Compositions

| Material | Function | Chemical nature | Supplier |
|---|---|---|---|
| NATROSOL ™ 250 HBR | Thickener | Hydrophobic modified cellulose | The Dow Chemical Company |
| Propylene Glycol | Solvent | Propylene glycol | |
| TRITON ™ BD-109 | Wetting agent | Nonionic surfactant | The Dow Chemical Company |
| TI-PURE R-902 | Pigment | Titanium dioxide | DuPont |
| CC-700 | Extender | Calcium carbonate | Guangfu Building Materials Group (China) |
| AMP-95 | Base | Organic amine neutralizer | ANGUS Chemie GmbH |
| OROTAN ™ CA-2500 | Dispersant | Hydrophobic modified dispersant | The Dow Chemical Company |
| NOPCO NXZ | Defoamer | Mineral Oil type | SAN NOPCO Ltd. |
| ROCIMA ™ 363 | Biocide | Biocide | The Dow Chemical Company |
| ROPAQUE Ultra E | Opaque polymer | Styrene polymer | The Dow Chemical Company |
| TEXANOL | Coalescent | Propanoic acid, 2-methyl-, monoester with 2,2,4-trimethyl-1,3-pentanediol | Eastman Chemical Company |
| ACRYSOL ™ RM-8W | Thickener | HEUR type | The Dow Chemical Company |
| ACRYSOL RM-2020 NPR | Thickener | HEUR type | The Dow Chemical Company |
| benzophenone | light initiator | light initiator | Sinopharm Chemical Reagent Co., Ltd. |

II. Analytical Method

To determine the DPUR level of a given aqueous coating composition sample, a DPUR test was conducted.

The aqueous coating composition sample was coated on asbestos by using a drawdown roller stick to form a 120 micron-thick wet film as a first layer. The coated asbestos was allowed to be cured in a consistent temperature room (23° C. and 50% relative humidity) for 4 hours. Then the aqueous coating composition sample was applied onto the first layer by using the drawdown roller stick to form an 80 micron-thick wet film as a second layer. The coated asbestos was allowed to be cured in the consistent temperature room (23° C. and 50% relative humidity) for 14 days. Then the coated asbestos was exposed to a QUV accelerated weathering tester equipped with UVA-340 nm lamps (QUV accelerated weathering tester: Model QUV/Spray; Irradiance 0.77 W/m²/nm) for 1 hour, 2 hours or 4 hours.

The DPUR level of the given aqueous coating composition sample is evaluated according to Item 5.4 (5.4.1.2 Method A) of the GB/T 9780-2013 standard: The GB/T 9780-2013 standard herein is the national standard for *Test method for dirt pickup resistance and stain removal of film of architectural coatings and paint*, which was published by General Administration of Quality Supervision, Inspection and Quarantine of the People's Republic of China (P. R. China) and Standardization Administration of the P. R. China, issued on Nov. 27, 2013, and put into effect on Aug. 1, 2014.

III. Sample Preparations

1. Synthesis of Inventive Benzophenone Derivatives

Inventive Benzophenone Derivative Compound A

Inventive Benzophenone Derivative Compound A was synthesized via the following procedure. 21.6 grams of 4-chloro benzophenone, 11.99 grams of 4-hydroxyaniliane, 0.56 grams of potassium hydroxide were added into 100 milliliters (ml) of NMP sequentially in a 250-ml vessel. The vessel was heated to a temperature of from 150° C. to 190° C. for around 12 hours. Then, the mixture in the vessel was cooled to room temperature. The solvent NMP was removed from the mixture by distillation under a reduced-pressure condition. 100 ml of toluene was then added into the mixture. The mixture was then washed by using a 50-ml 5% NaCl solution. The toluene was removed from the mixture by distillation under a reduced-pressure condition after a toluene layer was formed. 26.0 grams of an intermediate was obtained.

23.1 grams of the intermediate and 1.1 grams of potassium carbonate were added into 50 ml of chloroethanol in a 100-ml vessel. The vessel was heated to 70° C. for 5 hours before the mixture was cooled down to room temperature. The chloroethanol was then removed by distillation from the mixture under a reduced-pressure condition. Then the crude mixture was purified by recrystallization in ethanol solution. 20.5 grams of Inventive Benzophenone Derivative Compound A was then obtained.

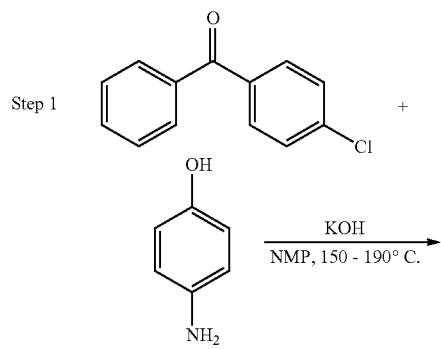

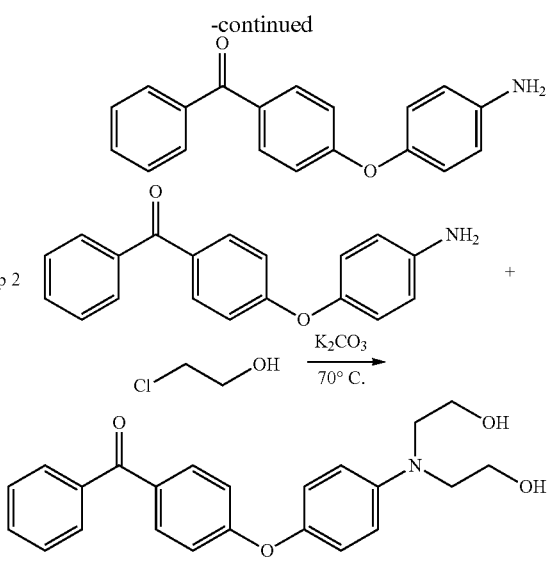

Inventive Benzophenone Derivative Compound B

Inventive Benzophenone Derivative Compound B was synthesized via the following procedure. 25.0 grams of 4,4'-dichloro benzophenone, 23.98 grams of 4-hydroxyaniliane, 0.56 grams of potassium hydroxide were added into 100 ml of NMP sequentially in a 250-ml vessel. The vessel was heated to a temperature of from 150° C. to 190° C. for around 12 hours. Then, the mixture in the vessel was cooled to room temperature. The solvent NMP was removed from the mixture by distillation under a reduced-pressure condition. 100 ml of toluene was then added into the mixture. The mixture was then washed by using a 50-ml 5% NaCl solution. The toluene was removed by distillation under a reduced-pressure condition after a toluene layer was formed. 35.0 grams of an intermediate was obtained.

31.68 grams of the intermediate and 1.1 grams of potassium carbonate were added into 50 ml of chloroethanol in a 100-ml vessel. The vessel was heated to 70° C. for 5 hours before the mixture was cooled down to room temperature. The chloroethanol was then removed by distillation from the mixture under a reduced-pressure condition. Then the crude mixture was purified by recrystallization in ethanol solution. 32.5 grams of Inventive Benzophenone Derivative Compound B was then obtained.

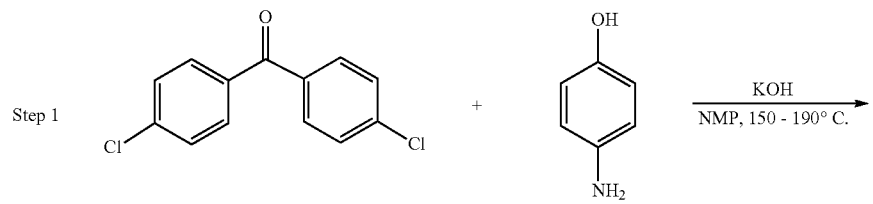

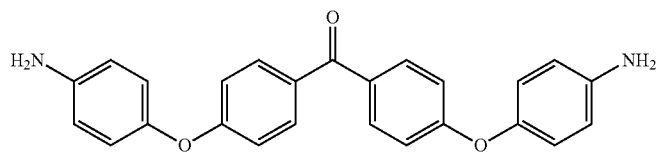

intemediate B

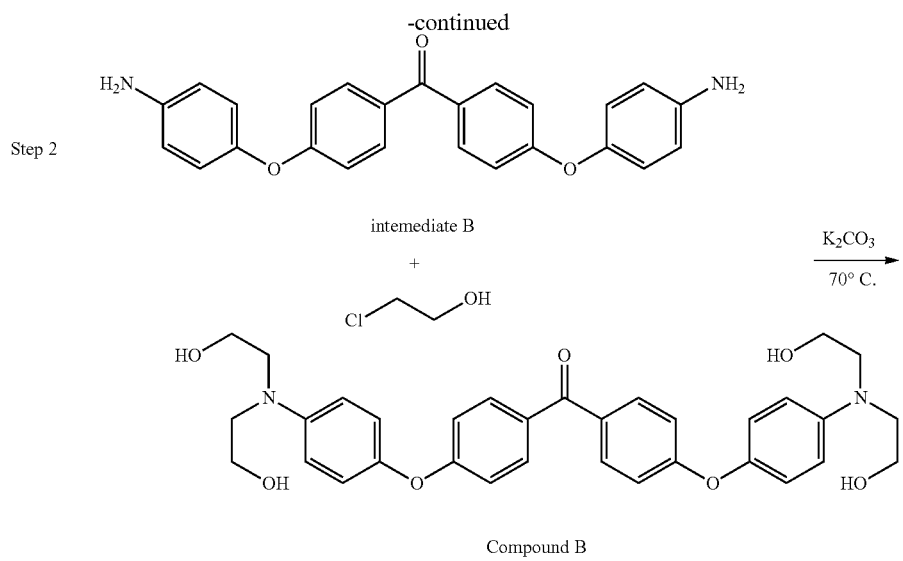

Step 2 intermediate B

Compound B

2. Preparation of Aqueous Copolymer Dispersions

Preparation of Inventive Aqueous Copolymer Dispersions

Inventive Aqueous Copolymer Dispersion 1: A solution was made by blending 1 gram of Inventive Benzophenone Derivative Compound A with 500 grams of PRIMAL AC-261P binder under agitation.

Inventive Aqueous Copolymer Dispersions 2 to 4 were prepared by using the same procedure as outlined for Inventive Copolymer Dispersion 1, except for the amounts of different benzophenone derivatives and binders being used. The amounts of various components (in grams) to make Inventive Copolymer Dispersions 1 to 4 are shown in TABLE 4 below.

Preparation of Comparative Aqueous Copolymer Dispersions

Comparative Aqueous Copolymer Dispersion 1: A solution was made by blending 1 gram of benzophenone with 500 grams of PRIMAL AC-261P binder under agitation.

Comparative Aqueous Copolymer Dispersion 2: A solution was made by blending 1 gram of benzophenone with 500 grams of ELASTENE 3808 binder under agitation.

The amounts of various components (in grams) to make Comparative Copolymer Dispersions 1 and 2 are shown in TABLE 4 below.

TABLE 4

| Aqueous Emulsions | Benzophenone Derivatives/ Benzophenone | Binders |
| --- | --- | --- |
| Inventive Aqueous Copolymer Dispersion 1 | 1 g Inventive Benzophenone Derivative compound A | 500 g PRIMAL AC-261P |
| Inventive Aqueous Copolymer Dispersion 2 | 1 g Inventive Benzophenone Derivative compound B | 500 g PRIMAL AC-261P |
| Inventive Aqueous Copolymer Dispersion 3 | 1 g Inventive Benzophenone Derivative compound A | 500 g ELASTENE 3808 |
| Inventive Aqueous Copolymer Dispersion 4 | 1 g Inventive Benzophenone Derivative compound B | 500 g ELASTENE 3808 |
| Comparative Aqueous Copolymer Dispersion 1 | 1 g benzophenone | 500 g PRIMAL AC-261P |
| Inventive Aqueous Copolymer Dispersion 2 | 1 g benzophenone | 500 g ELASTENE 3808 |

3. Preparation of Aqueous Coating Compositions

Inventive Aqueous Coating Composition 1

Inventive Aqueous Coating Composition 1 was made with a 48VS/40PVC (VS: volume solids) formulation using Inventive Aqueous Copolymer Dispersion 1.

Grind Phase: 150.0 grams of water, 15.0 grams of propylene glycol, 2.0 grams of NATROSOL 250 HBR thickener, 2.0 grams of AMP-95 base, 10.0 grams of OROTAN CA-2500 Dispersant, 2.0 grams of TRITON BD-109 wetting agent, 1.0 grams of NOPCO NXZ defoamer, 7.0 grams of ROCIMA 363 biocide, 150.0 grams of TI-PURE R-902 pigment, and 130.0 grams of CC-700 extender were added into a tank and stirred with a COWLES mixer under a high speed. The grind phase components were then well dispersed.

Letdown Phase: 380.0 grams of Inventive Aqueous Copolymer Dispersion 1, 50.0 grams of ROPAQUE Ultra E opaque polymer, 19.0 grams of TEXANOL coalescent, 5.0 grams of ACRYSOL RM-8W thickener, and 10.0 grams of ACRYSOL RM-2020 NPR thickener were then added to the tank and stirred with a conventional lab mixer (IKA mixer).

The amounts of the components (in grams) used in the grind phase and the letdown phase are shown in TABLE 5 below.

TABLE 5

| Inventive Aqueous Coating Composition 1 ||
| --- | --- |
| Material | Weight (gram) |
| Grind ||
| Water | 150.0 |
| Propylene glycol | 15.0 |
| NATROSOL 250 HBR | 2.0 |
| AMP-95 | 2.0 |
| OROTAN CA-2500 | 10.0 |
| TRITON BD-109 | 2.0 |
| NOPCO NXZ | 1.0 |
| ROCIMA 363 | 7.0 |
| TI-PURE R-902 | 150.0 |
| CC-700 | 130.0 |

TABLE 5-continued

Inventive Aqueous Coating Composition 1

| Material | Weight (gram) |
|---|---|
| Let down | |
| Inventive Aqueous Copolymer Dispersion 1 | 380.0 |
| ROPAQUE Ultra E | 50.0 |
| TEXANOL | 19.0 |
| ACRYSOL RM-8W | 5.0 |
| ACRYSOL RM-2020 NPR | 10.0 |
| Total | 930.0 |
| Paint characteristics | |
| Total PVC | 39.59% |
| Volume solids | 39.24% |
| Weight solids | 52.15% |

Inventive Aqueous Coating Compositions 2 to 4 and Comparative Compositions 1 and 2

Inventive Aqueous Coating Compositions 2 to 4 and Comparative Compositions 1 and 2 were prepared by using the same procedure outlined for Inventive Aqueous Coating Composition 1, except for the amounts of different aqueous copolymer dispersion and TEXANOL coalescent used in the letdown phase. The amounts of various aqueous copolymer dispersions and TEXANOL coalescent (in grams) used in the letdown phase for Inventive Aqueous Coating Compositions 2 to 4 and Comparative Compositions 1 and 2 are shown in TABLE 6 below.

TABLE 6

| Aqueous Coating Composition | Aqueous Copolymer Dispersion | TEXANOL |
|---|---|---|
| Inventive Aqueous Coating Composition 1 | 380 g Inventive Aqueous Copolymer Dispersion 1 | 19 g |
| Inventive Aqueous Coating Composition 2 | 380 g Inventive Aqueous Copolymer Dispersion 2 | 19 g |
| Comparative Aqueous Coating Composition 1 | 380 g Comparative Aqueous Copolymer Dispersion 1 | 19 g |
| Inventive Aqueous Coating Composition 3 | 380 g Inventive Aqueous Copolymer Dispersion 3 | 0 g |
| Inventive Aqueous Coating Composition 4 | 380 g Inventive Aqueous Copolymer Dispersion 4 | 0 g |
| Comparative Aqueous Coating Composition 2 | 380 g Comparative Aqueous Copolymer Dispersion 2 | 0 g |

IV. Summary of all Coating Compositions Analyzed

For purpose of demonstrating the superior properties of the aqueous coating compositions embodying the present invention, numerous coating samples with various combinations of key ingredients have been prepared and analyzed.

First, a comparison of DPUR performance was made between aqueous coating compositions prepared using the inventive benzophenone derivatives and those prepared using the conventional benzophenone. In particular, Inventive Aqueous Coating Compositions 1 to 4 were made from the inventive benzophenone derivative; whereas Comparative Aqueous Coating Compositions 1 and 2 were made from the conventional benzophenone.

Second, a comparison of UV initiator efficiency under different UV irradiation period was made between aqueous coating compositions prepared using the inventive benzophenone derivatives and those prepared using the conventional benzophenone.

V. Analytical Results

TABLE 7 below summarizes the DPUR levels of the inventive aqueous coating compositions (made with inventive benzophenone derivative) and the comparative aqueous coating compositions (made with the conventional benzophenone) determined according to the test method described above.

TABLE 7

DPUR Levels of Aqueous Coating Compositions

| Aqueous Coating Composition | UV Irradiation | DPUR (%) |
|---|---|---|
| Inventive Aqueous Coating Composition 1 | 4 hours | 10.0 |
| Inventive Aqueous Coating Composition 2 | 4 hours | 11.7 |
| Comparative Aqueous Coating Composition 1 | 4 hours | 13.0 |
| Inventive Aqueous Coating Composition 3 | 4 hours | 28.0 |
| Inventive Aqueous Coating Composition 4 | 4 hours | 32.4 |
| Comparative Aqueous Coating Composition 2 | 4 hours | 34.5 |
| Inventive Aqueous Coating Composition 3 | 1 hour | 12.6 |
| Comparative Aqueous Coating Composition 2 | 1 hour | 14.7 |
| Inventive Aqueous Coating Composition 3 | 2 hours | 11.0 |
| Comparative Aqueous Coating Composition 2 | 2 hours | 13.1 |

TABLE 7 shows that, for aqueous coating compositions that were made with PRIMAL AC-261P binder, those aqueous coating compositions that were made using the inventive benzophenone derivatives (Inventive Aqueous Coating Compositions 1 and 2) demonstrate a lower DPUR level (better DPUR performance) than that made using the conventional benzophenone (Comparative Aqueous Coating Composition 1); for aqueous coating compositions that were made with ELASTENE 3808 binder, those aqueous coating compositions that were made using the inventive benzophenone derivatives (Inventive Aqueous Coating Compositions 3 and 4) again demonstrate a lower DPUR level (better DPUR performance) than that made using conventional benzophenone (Comparative Aqueous Coating Composition 2).

TABLE 7 further shows that, under different UV irradiation period (1 hour, 2 hours and 4 hours), the aqueous coating composition that was made using the inventive benzophenone derivative (Inventive Aqueous Coating Composition 3) demonstrate a lower DPUR level (better DPUR performance) than that made using the conventional benzophenone (Comparative Aqueous Coating Composition 2) accordingly.

What is claimed is:

1. An aqueous copolymer dispersion comprising (a) an aqueous emulsion copolymer; and (b) from 0.05% to 3% by weight, based on the dry weight of the copolymer, of the benzophenone derivative represented by Formula A:

[Formula A]

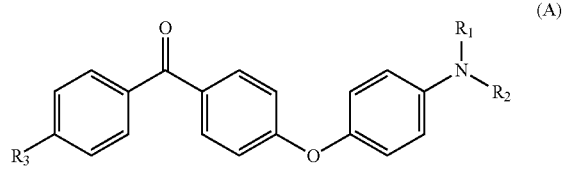

wherein $R_1$ and $R_2$ are independently an alkyl group or a substituted alkyl group, and $R_3$ is hydrogen or has a structure of Formula B:

[Formula B]

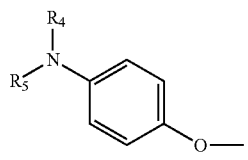
(B)

wherein $R_4$ and $R_5$ are independently an alkyl group or a substituted alkyl group.

2. The aqueous copolymer dispersion of claim 1, wherein the aqueous copolymer dispersion comprises from 0.2% to 0.8% by weight, based on the dry weight of the copolymer, of the benzophenone derivative.

3. The aqueous copolymer dispersion of claim 1, wherein the aqueous emulsion copolymer further comprises up to 5% by weight, based on the dry weight of the copolymer, of copolymerized multi-ethylenically unsaturated monomers.

4. The aqueous copolymer dispersion of claim 1, wherein the aqueous emulsion copolymer has a glass transition temperature of −70° C. to +70° C.

5. The aqueous copolymer dispersion of claim 1, wherein the aqueous emulsion copolymer comprises, as copolymerized units, at least 90% by weight, based on the dry weight of the copolymer, of an ethylenically unsaturated nonionic monomer; and up to 10% by weight, based on the dry weight of the copolymer, of an ethylenically unsaturated stabilizer monomer.

6. An aqueous coating composition comprising the aqueous copolymer dispersion of claim 1.

\* \* \* \* \*